United States Patent [19]
Rupp et al.

[11] Patent Number: 5,245,728
[45] Date of Patent: Sep. 21, 1993

[54] CLUMP DISSOLVING BAFFLE IN CONDUIT BETWEEN FLAKE SUPPLYING AND PAD FORMING DEVICES

[75] Inventors: Heinrich Rupp; Armin Geisen, both of Neuwied, Fed. Rep. of Germany

[73] Assignee: Winkler & Duennebier Maschinenfabrik und Eisengiesserei KG, Neuwied, Fed. Rep. of Germany

[21] Appl. No.: 888,523

[22] Filed: May 26, 1992

[30] Foreign Application Priority Data

May 27, 1991 [DE] Fed. Rep. of Germany ....... 4117252

[51] Int. Cl.⁵ .................... D01G 9/08; D01G 23/08; B27N 3/14; B02C 19/00
[52] U.S. Cl. ........................... 19/148; 19/308; 19/81; 264/121; 425/80.1
[58] Field of Search .................... 19/39, 48 R, 47, 52, 19/65 R, 65 A, 66 R, 82, 148, 145.5, 155, 156.4, 156.3, 200, 296, 304, 308; 241/70, 72, 73, 74, 57, 49, 79.2, 101.01, 191, 273.2, 273.3, 274, 291; 264/116, 121, 517, 518

[56] References Cited

U.S. PATENT DOCUMENTS

| | | | |
|---|---|---|---|
| 1,761,138 | 6/1930 | Lykken | 241/74 X |
| 1,834,309 | 12/1931 | Harney . | |
| 2,714,749 | 8/1955 | Clark et al. | 19/148 X |
| 2,807,054 | 9/1957 | Burger et al. | 264/518 |
| 2,940,133 | 6/1960 | Heritage | 19/156 |
| 2,940,134 | 6/1960 | Heritage | 19/156 |
| 2,940,135 | 6/1960 | Heritage | 19/156 |
| 3,016,906 | 1/1962 | Peters | 19/81 X |
| 3,233,836 | 2/1966 | Merges | 241/74 X |
| 3,576,349 | 4/1971 | Mark | 19/304 X |
| 3,886,629 | 6/1975 | Nakai et al. | 19/156.3 |
| 3,947,535 | 3/1976 | Bagg et al. | 264/517 X |
| 3,961,397 | 6/1976 | Neuenschwanser | 19/65 R |
| 4,375,447 | 3/1983 | Chung | 264/518 |
| 4,666,647 | 5/1987 | Enloe et al. | 19/148 X |
| 4,687,146 | 8/1987 | Sundman | 241/70 X |
| 4,859,388 | 8/1989 | Peterson et al. | 260/517 X |
| 4,931,243 | 6/1990 | Henschel et al. | 264/121 X |
| 5,044,052 | 9/1991 | Hertel et al. | 264/121 X |

FOREIGN PATENT DOCUMENTS

| | | | |
|---|---|---|---|
| 0273446 | 7/1988 | European Pat. Off. | 241/74 |
| 1111933 | 7/1961 | Fed. Rep. of Germany . | |
| 3031632 | 4/1982 | Fed. Rep. of Germany . | |
| 3731591 | 4/1989 | Fed. Rep. of Germany . | |
| 1186247 | 10/1985 | U.S.S.R. | 241/74 |
| 2010934 | 7/1979 | United Kingdom | 19/148 |
| 2134412 | 8/1984 | United Kingdom | 241/70 |

Primary Examiner—Clifford D. Crowder
Assistant Examiner—Ismael Izaguirre
Attorney, Agent, or Firm—W. G. Fasse

[57] ABSTRACT

Absorbent flakes or particles are transported from a source to a pad forming device by an air flow passing the flakes or particles through a conduit between the source and the pad forming device. In order to supply a homogenous flake flow to the pad forming device, baffle devices or at least one baffle device is arranged in the conduit. The baffle device or baffle devices are equipped with baffling rods arranged in a certain position within the baffling device housing so that the flake air mixture must flow through the spaces between neighboring baffling rods to assure a dissolution of any flake accumulations or clumps. Preferably, a cross-section flow area reducer is arranged upstream of each baffling device to increase the flow speed or velocity of the flow entering the respective baffling device.

26 Claims, 3 Drawing Sheets

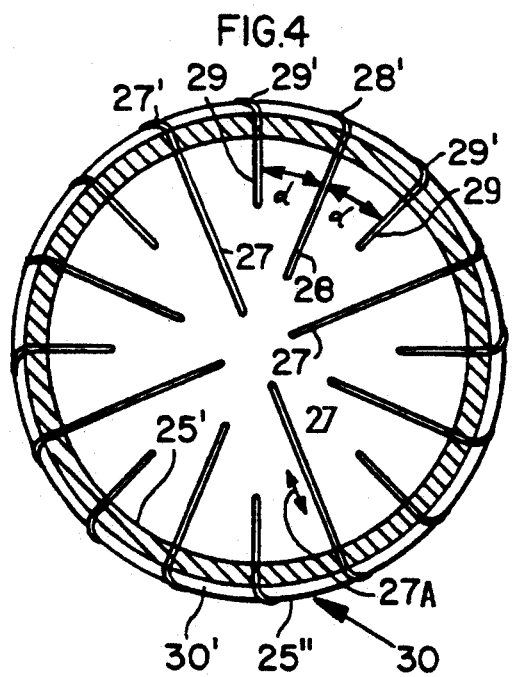
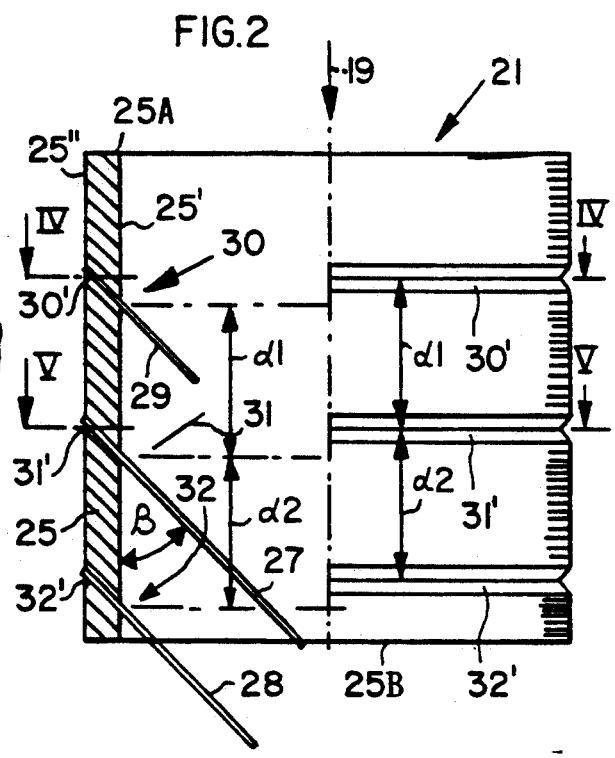
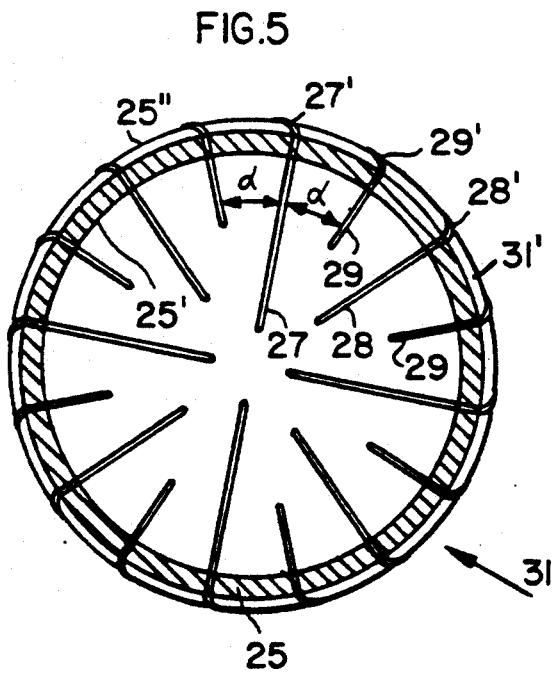
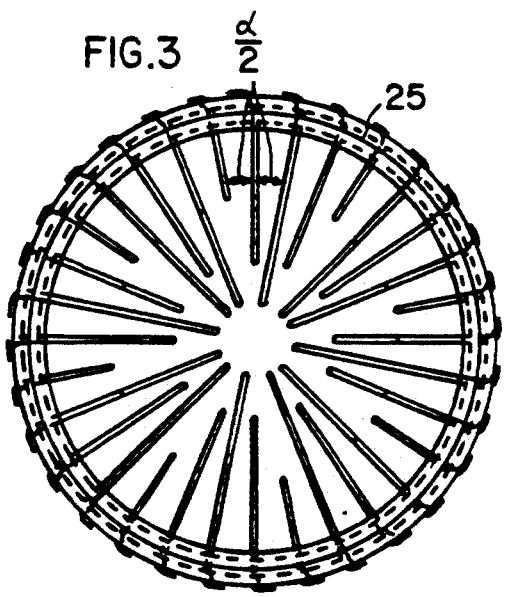

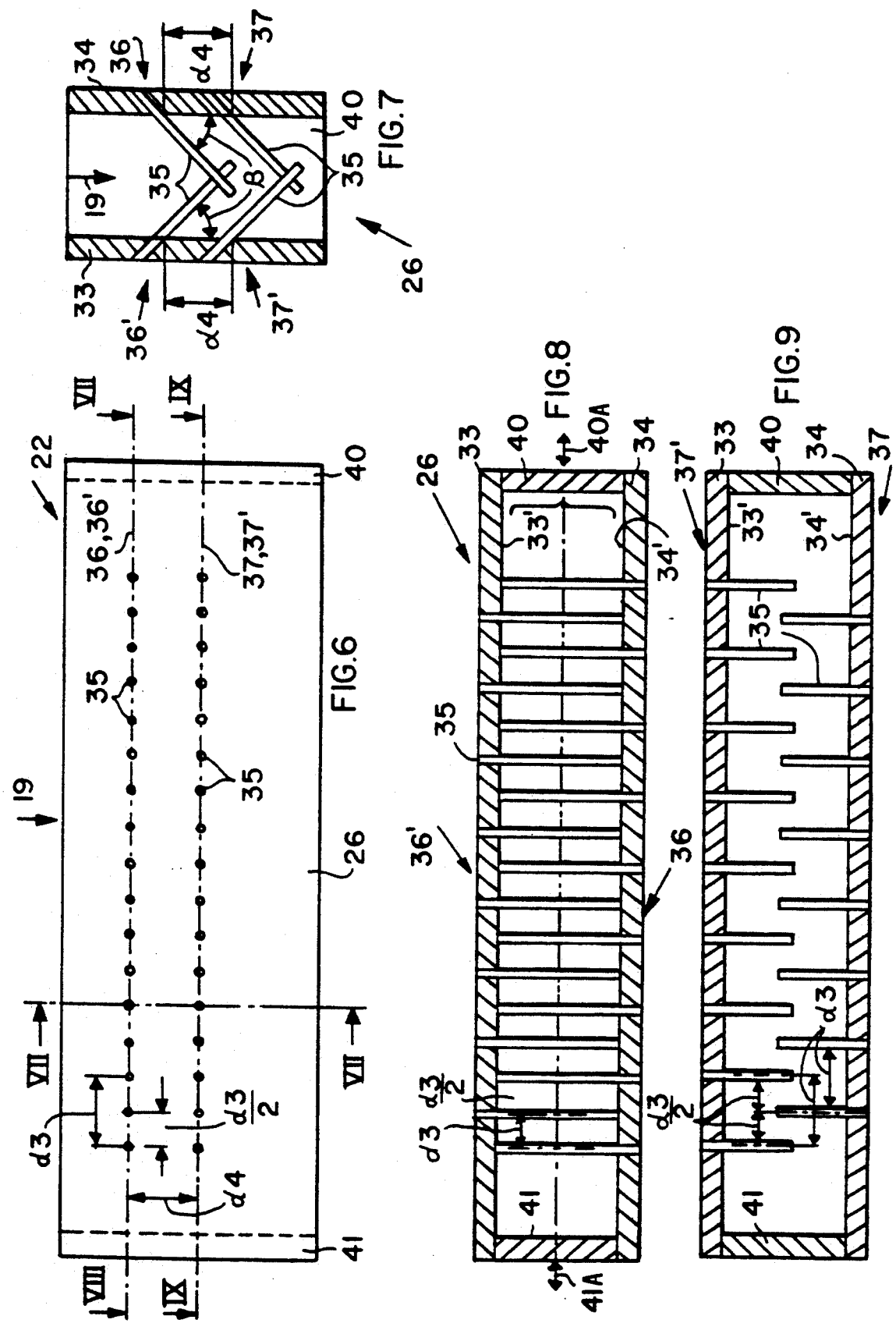

CLUMP DISSOLVING BAFFLE IN CONDUIT BETWEEN FLAKE SUPPLYING AND PAD FORMING DEVICES

FIELD OF THE INVENTION

The invention relates to an apparatus for dissolving clumps of flakes in a flake air mixture flow as such flow travels through a conduit from a flake supply to a flake pad forming device for the production of moisture absorbing flake pads.

BACKGROUND INFORMATION FOR THE INVENTION

Machines for the production of absorbent pads produce such pads by depositing hydrophilic particles or flakes on a support from which the pad is then transferred onto a substrate. The substrate with the absorbent pad deposited thereon is then used in the production of sanitary napkins, diapers, panties with absorbent inserts, fitted briefs, absorbent undergarments, and the like. The particles or flakes for this purpose are supplied from a source by an airstream flowing through a conduit to a flake pad former and depositor. The source of the flakes may be a fiber chopper to form particulate flake type material from a continuous web that is pulled off a supply reel.

In order to minimize adverse influences on the environment, including the work environment, and to protect the work place against excessive noise, it is now customary to separate the flake production facilities from the pad forming facilities. The two facilities are connected by a conduit in which a blower provides the necessary transporting air flow which intermixes with the produced flakes. Due to the length of the conduit, the internal friction between moving flakes and the inner surfaces of the conduit walls in combination with flow turbulences and static charges within the flake air mixture, there is a tendency to form nonuniform flake distributions and even flake clumps or bunched up balls of flakes. Such a nonuniform flake air flow is not suitable for the required homogenous flake distribution in the absorbent pads. A nonuniform flake distribution also adversely influences the stability of the flakes in a formed pad because flake bunches, although becoming part of the pad, are not properly bound into the pad, resulting in an inferior final product.

Efforts have been made heretofore to solve the problem of a uniform flake supply. For this purpose it is known to provide a positively driven milling rotor in the flake supply conduit. U.S. Pat. Nos. 1,834,309; 2,940,133; 2,940,134; 2,940,135; 3,886,629; and 4,375,447 relate to this technology. The provision of a positively driven milling rotor makes the supply conduit rather expensive. Besides, a substantial space is required for the installation of such rotors. The drive motor for these rotors must have a variable r.p.m. so that the r.p.m. can be adapted to the required through-put or through-flow of the flake air mixture per unit of time. Besides, such rotors produce undesirable air turbulences in the flow which again adversely affect the formation of a flake pad in which the flakes are uniformly distributed through the volume of the pad.

German Patent Publication DE 3,031,632 (Leifeld), published on Apr. 1, 1982, discloses an apparatus for cleaning and dedusting of textile fiber flakes. For this purpose, baffle grids or combs are positioned in the flow of the flake air mixture so as to function as filters or sieves which retain coarse particles while passing the airstream. Leifeld positions such a baffle comb (27, 27a) downstream of an injector nozzle (6, 7) as viewed in the flow direction. The purpose of these baffle combs is to deflect the flake air mixture toward sieves or grids (8, 8a) for the removal of dust from the flake air mixture.

German Patent Publication 1,111,933 (Chavannes et al.), published Jul. 27, 1961 discloses a method and apparatus for producing upholstery batting of cotton fibers or the like. The comminuted fibers travel on a conveyor belt that is air permeable through a chamber in which a synthetic material dust is injected into the cotton flake material This chamber is equipped with baffle plates (66) to diflect the airstream carrying the synthetic material dust in such a way that it must pass twice through the layer of batting and through the conveyor belt.

German Patent Publications DE 3,731,591 Al (Lucassen et al.), published on Apr. 6, 1989, discloses an apparatus for removing contaminations out of a fiber flow, especially spun fibers. For this purpose, guide combs (10, 11) are so arranged that they form an open rake (13, 14) which functions as a separator for the removal of the contaminations from the fiber flow. The flow of the fibers passes alongside of these combs or rakes.

OBJECTS OF THE INVENTION

In view of the foregoing it is the aim of the invention to achieve the following objects singly or in combination:

to provide an apparatus capable of dissolving any accumulations or bunching or clumps in a flowing flake air mixture so as to provide a uniform flake distribution downstream of the apparatus;

to provide a cost efficient, compact apparatus for the above purpose in which positively driven rotors are avoided by the use of stationary flake distribution elements forming a baffle device through which the flake air mixture must flow, whereby the flow dynamics of the flake air mixture are utilized for the dissolution of clumps and for the uniform distribution of the flakes in the flow; and to obtain ever better working results as the flow speed and thus the through-put quantity per unit of time increases by the use of the flow dynamics of the flow itself for dissolving clumps.

SUMMARY OF THE INVENTION

The apparatus according to the invention is characterized by at least one flow baffling device arranged in a flow conduit so that the flake air mixture flow must pass through the baffling device which comprises a plurality of stationary baffling elements reaching into the flow to cause the flow to pass through gaps in the baffling device to achieve an efficient fluffing-up.

The main advantage of the of the invention is seen in that the baffling elements themselves are in a stationary position inside the baffling device which itself may be vibrated. This construction results in a cost effective compact device in which flake bunches or clumps are efficiently dissolved by the inherent flow dynamic of the flake air mixture It has been found that the efficiency of the device keeps increasing as the through-put quantity per unit of time of the flake air mixture through the baffling device increases. This is an unexpected result.

BRIEF DESCRIPTION OF THE DRAWINGS

In order that the invention may be clearly understood it will now be described, by way of example, with reference to the accompanying drawings, wherein:

FIG. 2 is a side view, partially in section, of a baffling device according to the invention, having a circular cross-section;

FIG. 3 is a view in the direction of the arrow (19) in FIG. 2, whereby the arrow (19) indicates the flow direction of the flake air mixture;

FIG. 4 is a sectional view along section line IV—IV in FIG. 2;

FIG. 5 is a sectional view along section line V—V in FIG. 2;

FIG. 6 is a side view of a second embodiment of a baffling device according to the invention having a rectangular configuration;

FIG. 7 is a sectional view along section line VII—VII in FIG. 6;

FIG. 8 is a sectional view along section line VIII—VIII in FIG. 6; and

FIG. 9 is a sectional view along section line IX—IX in FIG. 6.

DETAILED DESCRIPTION OF PREFERRED EMBODIMENTS

Figure 1:
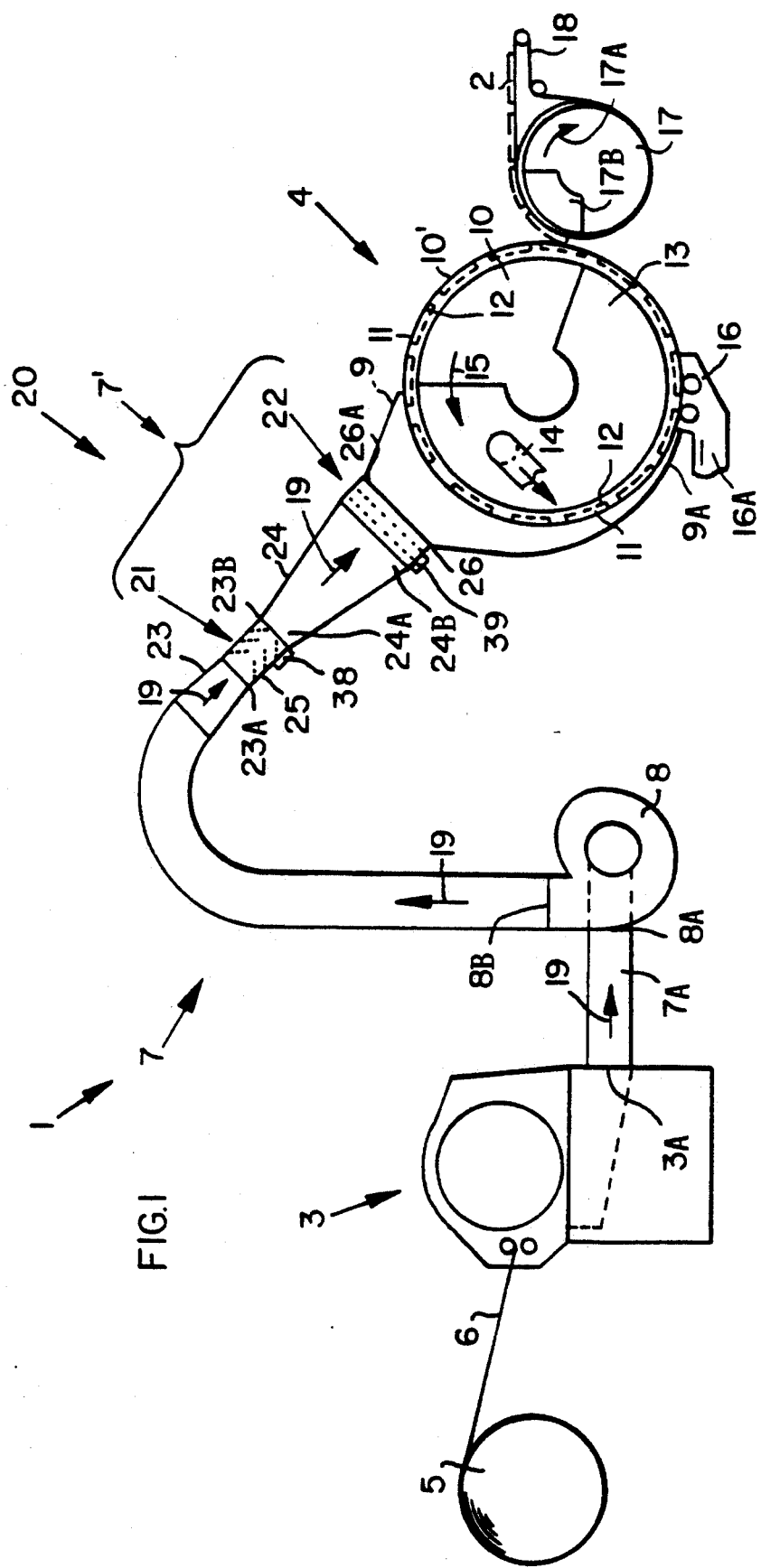
FIG. 1 is a schematic side view of a machine for producing absorbent pads in which the flow conduit for the supply of a flake air mixture is equipped with baffle devices according to the invention.

FIG. 1 shows the installation of both types of baffling devices in the supply conduit. However, one or the other baffling device may be used alone for the present purposes.

The production system 1 shown in FIG. 1 comprises a supply reel 5 of a web 6 of absorbent cellular material, such as cotton batting or a layer of pulp material The web or layer 6 is fed into a chopper 3, the output 3A of which is connected through a conduit section 7A to the suction inlet 8A of a blower 8. The output 8B of the blower 8 is connected through a conduit 7 to a so-called flake box 9 of a pad forming depositor wheel or drum 10. The blower 8 forms a flake air mixture that passes through the conduit 7 in the flow direction 19. The flake box 9 surrounding partially the pad forming depositor wheel 10 and a suction device 14 as well as a brush-off unit 16 form together the flake pad former and depositor unit 4. The wheel comprises a cylindrical drum housing 10' rotating in the direction of the arrow 15. The drum 10' comprises in its surface molds 11 equipped with sieve bottoms 12. These molds are exposed to suction through the sieves 12. The suction is produced by the suction device 14 connected to a stationary suction box 13 communicating with the molds 11 through the sieves 12. Thus, suction begins to be applied to the molds when they enter the flake box 9 and suction stops, when the formed pads 2 are to be transferred onto a conveyor belt 18 running around a suction cylinder 17 which causes the transfer of the pads 2 out of the molds 11 onto the air permeable conveyor belt 18. The suction cylinder 17 rotates as indicated by the arrow 17A and has a stationary suction box 17B which also limits the application of suction to the transfer area.

The pads are formed by drawing flakes into the molds 11 with the suction generated in the suction box 13 by the suction device 14. The screens or sieves 12 separate the flakes from the transporting air so that the flakes are densified in the mold 11 until a suction pad 2 is formed. Immediately downstream of the lower end 9A of the flake box 9 there is the brush-off unit 16 which levels the flakes in the molds 11 so that each pad has the same thickness. The unit 16 functions as a screeding device and removes any flakes that project outside the cylinder plane defined by the drum 10'. These excess flakes are transported through a duct 16A back into the chopper 3. Downstream of the brush-off unit 16 there is arranged the above mentioned suction cylinder 17 which removes the pads 2 from the molds 7 and deposits these pads 2 on the conveyor belt 18. The belt 18 conveys the pads 2 to further production machinery not shown since such machinery is not part of the invention.

For achieving a high flake distribution quality throughout the volume of the pads 2, it is necessary to supply a uniform flake flow to the molds 11. For this purpose the invention provides at least one, preferably two, baffle devices 21, 22 in the end section 7' of the duct 7 just upstream of the flake box 9. The first baffle device 21 is shown in more detail in FIGS. 2, 3, 4, and 5, whereby FIG. 3 is a view superimposing FIGS. 4 and 5. The second baffling device 22 is shown in more detail in FIGS. 6, 7, 8, and 9.

Just upstream of the baffling device 21 there is a cross-sectional flow area reducer pipe section 23 for increasing the flow speed into the baffling device 21. Similarly, a cross-sectional flow area reducer 24 is arranged between the baffling device 21 and the baffling device 22. Since the baffling device 22 has a rectangular cross-section, the reducer 19 also functions as an adapter between the circular exit of the device 21 and the rectangular inlet of the device 22.

Referring to FIGS. 2, 3, 4, and 5 in conjunction, the baffling device 21 comprises a tubular pipe section 25 with an inlet end 25A and an outlet end 25B. The pipe section 25 has a circular cross-section, whereby the inlet end 25A matches to the output of the flow area reducer 23. A flexible collar 23A may be provided between the outlet of the reducer 23 and the inlet of the pipe section 25. Similarly, a flexible collar 23B may be provided between the outlet 25B and the inlet 24A of the second reducer and adapter 24. According to the invention, stationary baffling elements in the form of rods 27, 28, and 29 extend inwardly with their free ends out of the inner surface 25' of the pipe section 25. Three circular rows 30, 31, and 32 of baffling rods are arranged inside the tube. An axial spacing d1 is provided between the row 30 and the row 31. An axial spacing d2 is provided between the row 31 and the row 32 as shown in FIG. 2. The rods 27, 28, 29 slant radially inwardly.

As shown in FIG. 2, each of the baffle elements or rods 27, 28, and 29, extends at an angle $\beta$ relative to the inner surface 25' of the pipe section 25 into the interior of the pipe section 25. All baffle rods extend inwardly with their free ends in the pattern shown in FIG. 3, 4, and 5. Additionally, the neighboring rods, as viewed in the circumferential direction, are spaced from each other by an angle $\alpha$, as shown in FIGS. 4 and 5. The angle $\alpha$ is the same in all rows 30, 31, and 32 for all baffle rods 27, 28, and 29, so that a uniform distribution is achieved. Further, the arrangement is such that between two long baffle rods 27, which are spaced, for example, by 90° in the circumferential direction, there is arranged a baffle rod 28 of intermediate length at 45°, and two short baffle rods 29 are again arranged centrally between a long rod 27 and an intermediate length rod 28 so that the spacing $\alpha$ is 22.5°.

Further, the rods in one circular row are staggered relative to the rods in the other circular row in the circumferential direction by an angle $$\frac{\alpha}{2}$$

corresponding to 11.25° as shown in FIG. 3. As a result, the short baffle rods 29 of the circular row 30 register with the long rods 27 in the row 31 and with the half long rods 28 in the row 32 as seen in FIG. 2. This registering of the rods is viewed in the axial longitudinal direction of the pipe section 25.

In order to avoid the crowding of the rods centrally in the pipe section, it is necessary to provide the different lengths for the several rods as described above. As is shown in FIG. 3, the circumferential spacings forming through-flow openings, are approximately the same between the neighboring rods 27, 28, 29 in the circular rows 30, 31, and 32. These through-flow openings are so dimensioned that they are smaller than the largest flake accumulations or concentrations still permissible or acceptable for incorporation into the pads 2 to properly dissolve clumps that are too large. As seen in FIGS. 3, 4, and 5, the spacings between the rods become narrower radially inwardly.

FIG. 2 shows that the individual baffle rods 27, 28, 29, pass through respective angled bores in the wall of the pipe section 25. The respective angle of the bores corresponds to the angle $\beta$. The bores begin in circumferential outer grooves 30', 31', and 32' so that outer end hooks 27', 28', and 29' may be anchored in the circumferential grooves 30', 31', 32' which are formed in the outside surface 25" of the pipe section 25.

The effective length of the individual baffle rods inside the pipe section 25 can be varied by providing a relatively tight sliding fit of the rods in their respective bores through the wall of the pipe section 25 so that the insertion of the rods can be controlled by inserting these rods more or less as indicated by the double arrow 27A similar to the insertion of a dipstick.

Referring to FIGS. 6, 7, 8, and 9, the second embodiment of the present baffling device 22 will now be described. As mentioned, the flow cross-section reducer and adapter has a circular inlet end 24A that may be provided in the form of a flexible collar, and a rectangular outlet end 24B that may also be provided as a flexible collar for permitting the vibration of the devices 21 and 22 as will be described in more detail below.

As best seen in FIG. 7, two rows of baffle rods 35 are arranged on each side of the walls 33 and 34 of the housing 36 of the baffle device 22. The rods extend with their free ends at an angle $\beta$ relative to the inner wall surface of the housing 36 and point partially in the direction 19 of the flake air mixture flow. The walls 33 and 34 and thus the inner surfaces 33' and 34' of the rectangular housing 26 extend in parallel to each other. The row 36 of rods 35 and the row 36' of rods 35 extend at a common level while the rows 37 and 37' extend at a downstream level. The two levels are spaced from each other by a spacing d4 as best seen in FIGS. 6 and 7. Here again, the rods 35 extend through respective bores in the side walls and a tight fit may be provided for inserting the rods more or less deep into the space of the housing 26. The spacing between rods neighboring in the same row is again d3, while a spacing between neighboring rods in opposite rows is $$\frac{d3}{2}$$

as best seen in FIGS. 6, 8, and 9. The arrangement is such, that there is a partial overlap as shown in FIG. 7. The spacing $$\frac{d3}{2}$$

is selected so that this spacing is smaller than the largest permissible accumulation of flakes and so that jamming of flakes between the baffle rods is nevertheless prevented to assure a continuous free flow through the volume of the baffling device 22. Components 21, 22, 23 and 24 form a flake bunching preventer 20.

The flake bunching preventer 20 according to the invention which comprises either the baffling device 21 and the baffling device 22 or one of these baffling devices, preferably with a respective cross-sectional flow area reducer 23, 24, operates as follows. The flake air mixture flow travels in the direction 19 through the conduit 7 and through the preventer 20. The travelling speed causes the accumulations or bunches of flakes to impinge on the baffle rods 27, 28, 29, 35 with a sufficient impact force to dissolve these flake accumulations.

Due to the arrangement of several circular rows 30, 31, 32 or linear rows 36, 36', 37, 37' of baffle rods 27, 28, 29 or 35 in the flow direction, one behind the other, the number of impingement by flake accumulations on these baffle rods is increased without effectively reducing the free cross-sectional flow area through these baffle devices 21, 22, and without noticeably increasing the flow resistance or drag through these devices 21, 22. The spacings d1, d2, and d4 are so dimensioned that any slow-down in the flow velocity of flake accumulations by an upstream row 30, 31, or 36, 36' of baffle rods is made up again before the flow of the flake air mixture reaches the next row 31, 32 or 37, 37' of rods. In other words, these spacings should be sufficient to permit the renewed acceleration of the flow from a slow-down caused by an upstream row of baffle rods before the flow reaches the next flow of baffle rods further downstream. The renewed acceleration should be sufficient to cause the dissolution of flake clumps that may have succeeded to pass the baffle rods further upstream as viewed in the flow direction.

Although in FIGS. 3, 4, and 5 showing the embodiment with a conduit having a circular cross-section, the free ends of the rods 27, 28, 29 slant radially inwardly, the rods 35 in the embodiment with a rectangular cross-section shown in FIGS. 6, 7, 8, and 9 extend in parallel to each other while also slanting inwardly.

On the other hand, the spacings d1, d2, and d4 should be sufficiently short to make sure that any flake accumulations or clumps in fact impinge on the baffle rods. For this purpose it is preferred that upstream of each of the baffling devices 21, 22, a cross-sectional flow area reducer 23, 24 is arranged as described above. The reduction of the cross-sectional flow area increases the flow speed, thereby enhancing the dissolution of flake clumps.

The slanting angle $\beta$ of the rods 27, 28, 29 relative to the inner surface 25' of the embodiment of FIG. 2 and the same angle $\beta$ of the rods 35 relative to the housing walls 33', 34' of FIG. 7 is so selected that on the one hand, jamming of flakes in the baffle devices 21, 22 is avoided, and that on the other hand, the flake accumulations find sufficient resistance to be dispersed or dissolved. For practical purposes the angle β should be within the range of about 30° to about 55°. The flow speed, again for practical reasons, should be within the range of about 20 m/s to about 35 m/s.

Referring again to FIG. 1, the baffle device 21 is equipped with a vibrator 38 and the baffle device 22 is equipped with a vibrator 39. Although the individual baffle rods are stationary relative to their respective housing, the efficiency of these devices 21, 22 is increased by vibrating the entire device. Such vibrating also improves the flake quality. It has been found that the inclination angle β can be increased when the entire device 21, 22 is vibrated without encountering any jamming within these devices.

Depending on the characteristics of the flake material, and on the flow velocity through the conduit 7, it is practical to make the spacings d1, d2, d3, and d4 variable. Similarly, the angle α and/or the angle β could be variable by respectively constructing the baffle rods to be adjustable in their position. It is also feasible to keep on hand a number of baffle devices 21, 22 of identical dimensions, but differently positioned baffle rods so that these devices can be readily exchanged against one another for handling different types of flakes. For example, the flow cross-sectional area inside of the baffling device 22 could be reduced by pushing the lateral end walls 40, 41 of the housing 26 inwardly between the longitudinal walls, or rather, between the side walls 33, 34, as shown by arrows 40A, 41A. The increase in the flow speed results in a corresponding increase in the efficiency of homogenizing the flake air mixture passing through the baffling devices.

FIGS. 2 and 6 show baffling rods 27, 28, 29, and 35 which have a circular cross-section. Such rods are most cost efficient. However, it is quite possible to use for special purposes baffling rods having, for example, an elliptical, a triangular, or a rectangular or square cross-section.

Rather than mounting the baffle rods to an external housing wall as shown in present FIGS. 2 to 9, it is also possible to mount the baffling rods to a central shaft which in turn is mounted centrally in the pipe section 25 or in the housing 26. The baffle rods would then be directed outwardly from the center, rather than inwardly toward the center as shown. The function would be the same in both instances.

Although the invention has been described with reference to specific example embodiments it will be appreciated that it is intended to cover all modifications and equivalents within the scope of the appended claims.

What is claimed is:

1. An apparatus for dissolving accumulations of flakes within a flake air mixture, said apparatus comprising a conduit for connecting a flake producing device to a flake pad former and depositor, said flake air mixture passing through said conduit in a flow direction from said flake producing device to said flake pad former, said apparatus further comprising at least one flow baffling device positioned in said conduit, said flow baffling device comprising stationary baffling members for preventing flake bashing and for dissolving said flake accumulations, said baffling members having free ends extending inwardly to form flow gaps inside said baffling device in said conduit so that said flake air mixture must pass through said flow gaps, said free ends of said baffling members extending partly in said flow direction.

2. The apparatus of claim 1, wherein said flow baffling device is positioned in an end section of said conduit upstream a flake box of said flake pad former and depositor.

3. The apparatus of claim 1, wherein said conduit comprises a pipe section, said baffling members projecting with said free ends inwardly from an inner wall surface of said pipe section.

4. The apparatus of claim 1, wherein said baffling members comprise baffling rods in said baffling device.

5. The apparatus of claim 4, wherein said free ends of said baffling rods are spaced from one another by a predetermined spacing angle α in a circumferential direction, and wherein said free ends of said baffling rods slant radially inwardly toward a central axis of said baffling device.

6. The apparatus according to claim 4, wherein said baffling rods extend at an acute angle of inclination β inwardly of said baffling device relative to an inner surface of said baffling device and as viewed in a flow direction of said flake air mixture flow.

7. The apparatus of claim 4, wherein said baffling rods of said baffling device form a number of rows along an inner wall surface of said baffling device.

8. The apparatus of claim 7, wherein said rows of baffling rods comprise a first row of baffling rods and a second row of baffling rods spaced from each other by a first spacing (d1), and a third row of rods spaced from said second row of rods by a second spacing (d2).

9. The apparatus of claim 8, wherein said baffling rods of said first, second and third rows of baffling rods are spaced relative to each other in a circumferential and axial direction by a predetermined spacing angle $$\frac{\alpha}{2}.$$

10. The apparatus of claim 8, wherein said first spacing (d1) and said second spacing (d2) are variable.

11. The apparatus of claim 7, wherein neighboring rows of baffling rods are staggered relative to each other by a spacing corresponding to one half of a spacing (d3) between neighboring baffling rods.

12. The apparatus of claim 7, wherein si baffling rods form two rows spaced from each other by a predetermined spacing (d4).

13. The apparatus of claim 4, wherein said baffling rods form groups of baffling rods, such that each group has baffling rods of a different length compared to the other groups of baffling rods.

14. The apparatus of claim 4, wherein neighboring baffling rods, arranged in said row, have a spacing (d3) from each other.

15. The apparatus of claim 4, wherein said baffling rods comprise a sliding fit in said conduit for adjusting an effective length of said baffling rods.

16. The apparatus of claim 1, further comprising a vibration generator (38, 39) connected to said baffling device for vibrating the entire baffling device.

17. The apparatus of claim 16, wherein said vibration generator, attached to said baffling device, imparts a rotational vibration to said baffling device.

18. The apparatus of claim 16, wherein said vibration gener

19. The apparatus of claim 1, further comprising releasable collars connecting said baffling device to said conduit.

20. The apparatus of claim 1, further comprising means for reducing the cross-sectional flow area of said conduit, said means being positioned just upstream of said baffling device as viewed in the flow direction of said flake air mixture flow for increasing the flow speed of said flake air mixture into said baffling device.

21. The apparatus of claim 20, wherein said baffling device comprises means for varying the flow cross-sectional area through said baffling device.

22. The apparatus of claim 1, further comprising a central carrier shaft mounted in said baffling device, said stationary baffling members being secured to said central carrier shaft to extend radially inwardly and.

23. The apparatus of claim 1, wherein said flow gaps formed by said free ends of said baffling members become narrower radially inwardly.

24. The apparatus of claim 1, wherein said conduit has a rectangular cross-section, and wherein said baffling members extend with their free ends into said rectangular cross-section from opposite sides of said conduit so that said free ends overlap.

25. The apparatus of claim 24, wherein said baffling members extend in parallel to each other.

26. An apparatus for dissolving accumulations of flakes within a flake air mixture, said apparatus comprising a conduit for connecting a flake producing device to a flake pad former and depositor, said flake air mixture passing through said conduit in a flow direction from said flake producing device to said flake pad former, said apparatus further comprising at least one flow baffling device positioned in said conduit, said flow baffling device comprising stationary baffling members for preventing flake bushing and for dissolving said flake accumulations, said baffling members forming flow gaps inside said baffling device so that said flake air mixture must pass through said flow gaps, and wherein said baffling members comprise baffling rods forming a number of rows at least along an inner wall surface of said conduit.

* * * * *

UNITED STATES PATENT AND TRADEMARK OFFICE
CERTIFICATE OF CORRECTION

PATENT NO. : 5,245,728
DATED : September 21, 1993
INVENTOR(S) : Heinrich Rupp et al.

It is certified that error appears in the above-identified patent and that said Letters Patent is hereby corrected as shown below:

On the title page, [75] should read:
 --Heinrich Rupp, Moenchengladbach, Fed. Rep. of Germany
   Armin Geisen, Neuwied, Fed. Rep. of Germany--;

Column 7, line 66, replace "bashing" by --bunching--;

Column 8, line 27, after "of" (2nd occurrence) insert --circular--

Column 8, line 48, replace "si" by --said--;

Column 9, line 16, delete "and";

Column 10, line 15, replace "bushing" by --bunching--.

Signed and Sealed this

Eighth Day of March, 1994

Attest:

BRUCE LEHMAN

Attesting Officer

Commissioner of Patents and Trademarks